United States Patent [19]

Lopez-Meroño

[11] 3,950,410

[45] Apr. 13, 1976

[54] OXIDATION PROCESS

[75] Inventor: José Lopez-Meroño, Stockton-on-Tees, England

[73] Assignee: Imperial Chemical Industries Limited, London, England

[22] Filed: Mar. 13, 1974

[21] Appl. No.: 450,885

Related U.S. Application Data

[63] Continuation-in-part of Ser. No. 257,574, May 30, 1972, abandoned.

[30] Foreign Application Priority Data

June 4, 1971 United Kingdom............... 19009/71

[52] U.S. Cl............................ 260/531 R; 260/537 P
[51] Int. Cl.² ......................................... C07C 51/26
[58] Field of Search...................... 260/531 R, 537 P

[56] References Cited
UNITED STATES PATENTS

| | | | |
|---|---|---|---|
| 2,193,562 | 3/1940 | McAllister | 260/531 R |
| 2,578,306 | 12/1951 | Hull | 260/531 R |
| 3,637,832 | 1/1972 | White et al. | 260/531 R |
| 3,761,517 | 9/1973 | Rohl et al. | 260/531 R |

Primary Examiner—Lorraine A. Weinberger
Assistant Examiner—P. J. Killos
Attorney, Agent, or Firm—Cushman, Darby & Cushman

[57] ABSTRACT

In the oxidation of a liquid alcohol and/or ketone with nitric acid to a carboxylic acid, especially of a mixture of cyclohexanol and cyclohexanone to adipic acid, temperature is controlled during the reaction in which gas is evolved by contacting the reaction mixture with a plurality of cooling surfaces vertically spaced from each other in such a way that the turbulence induced by the reaction inhibits the formation of bubbles upon the cooling surfaces. The cooling surfaces may be horizontally disposed banks of tubes through which water is passed.

4 Claims, 2 Drawing Figures

U.S. Patent  April 13, 1976  3,950,410
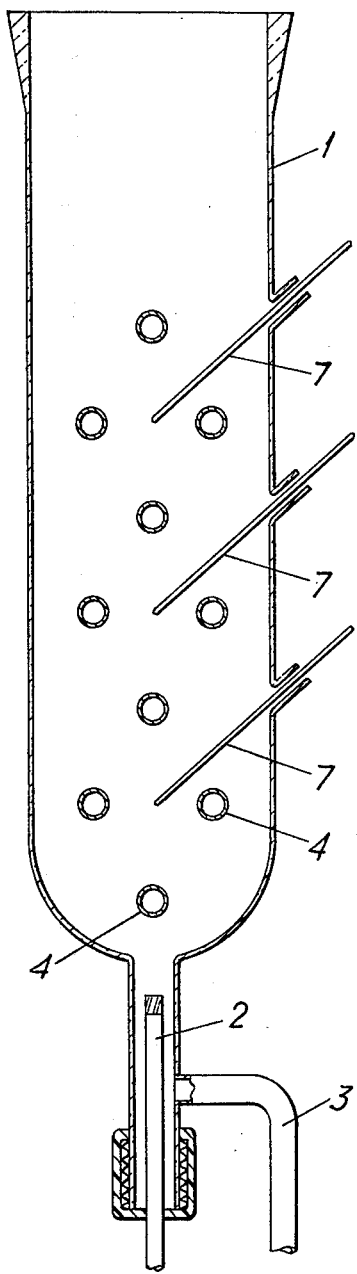
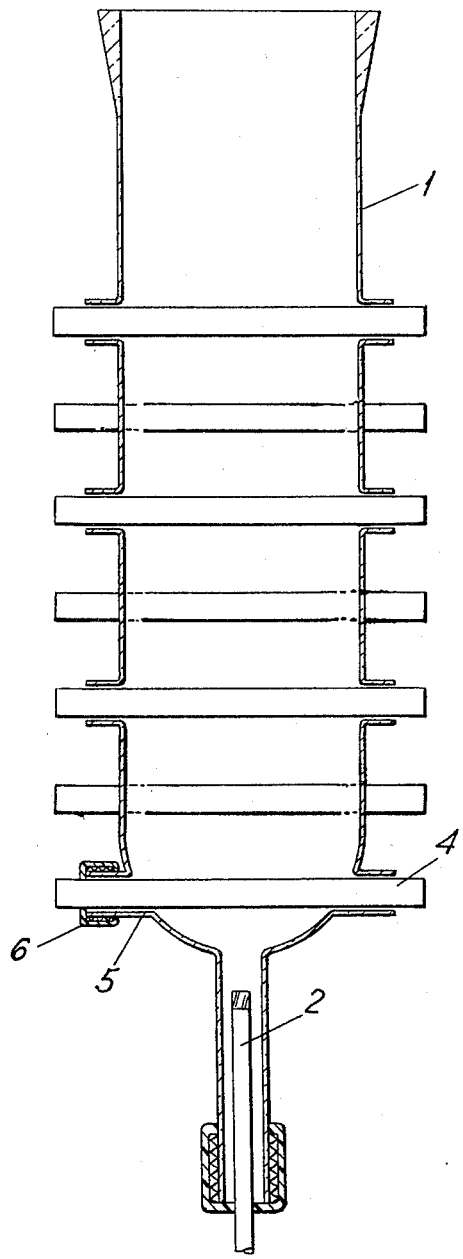

OXIDATION PROCESS

This application is a continuation-in-part of my application Ser. No. 257,574 filed May 30, 1972, now abandoned, for Oxidation Process.

This invention relates to an oxidation process and, more particularly, to a process for producing adipic acid.

Adipic acid, an intermediate used in the manufacture of nylon 6,6 (hexamethylenediamine adipamide), is currently manufactured by oxidising with nitric acid the mixture of ketone and alcohol (designated "KA") obtained by oxidation of cyclohexane with an oxygen-containing gas. This nitric acid oxidation is extremely exothermic and in continuous operation it has hitherto been found necessary to circulate liquid through external coolers in order to control the vigour of the reaction. Deposition of bubbles on internal cooling surfaces has reduced the overall heat transfer coefficient so much that it has not been found possible to control the reaction by means of internal cooling surfaces only.

The present invention provides, in a process for producing a carboxylic acid by oxidising a liquid alcohol and/or ketone with nitric acid, the method of controlling the reaction temperature which comprises bringing a mixture of nitric acid with alcohol and/or ketone, while still undergoing reaction in a vessel and thereby evolving gas, into contact with a plurality of cooling surfaces disposed within said vessel in vertically spaced formation from each other, the interspacing of said surfaces being such that the turbulence induced by the reaction inhibits the formation of bubbles upon the cooling surfaces.

The invention is of particular value in the oxidation of cyclohexanone and/or cyclohexanol with nitric acid to produce adipic acid. Mixtures of cyclohexane with oxygen-containing gases, and typically containing from 5 to 60% by weight of cyclohexanone are of special interest as starting materials. If desired the reaction may be conducted in presence of a catalyst, for example a mixed copper/vanadium catalyst.

The strength and amount of nitric acid for particular oxidations are already known in the art. For the oxidation of KA, nitric acid of strength 40 to 60% by weight may conveniently be used, the proportion by weight relative to KA being, for example, from 7:1 to 30:1, and more particularly from 8:1 to 15:1.

The process of the invention is particularly adaptable to continuous operation by passing ketone and/or alcohol into a vessel containing the internal cooling surfaces and taking the mixture from the vessel when interaction is complete.

Although various designs of cooling elements may be used, subject to the requirement that there must be sufficient vertical spacing between cooling surfaces, the invention operates best using horizontally disposed banks of tubes, preferably of substantially circular cross section. For efficient operation the overall height of the cooling elements in the vessel should be from 20 to 60 c.m., especially 30 to 45 cm. With smaller heights, the cooling is generally inadequate for continuous operation, and with greater heights crystallisation of carboxylic acid (e.g. adipic acid) may occur. A cooling fluid, conveniently water, is passed through the tubes. Provided these conditions relating to the height of the cooling elements are observed, the length and breadth of the cooling elements and the shape of the vessel within which they are contained is immaterial.

Conditions for efficient operation to oxidise KA in a continuous process can be defined in terms of a parameter $k$ representing the number of kilos of KA passing through the vessel per hour for each square meter of cooling surface. Efficient operation takes place within a range of $k$ values from 10 to 60. Preferred values of $k$ are from 20 to 40 and the process operates best when K is about 30.

When the cooling elements comprise banks of horizontally disposed tubes the external diameter of these should preferably be from 0.3 to 10 cm. and the distance in centimeters between the banks of tubes and between the tubes themselves should preferably be within the limits $0.04\ k$ to $0.20\ k$, and more preferably within the limits $0.08\ k$ to $0.12\ k$ where $k$ is the parameter already defined.

It will be appreciated from the foregoing that the present invention provides an improvement in a process for producing adipic acid by oxidising with nitric acid a liquid mixture of cyclohexanol and cyclohexanone, the improvement comprising controlling the reaction temperature by bringing a mixture of nitric acid with a liquid mixture of cyclohexanol and cyclohexanone, while still undergoing reaction in a vessel and thereby evolving gas, into contact with a plurality of cooling surfaces disposed within the vessel in vertically spaced formation from each other and consisting of horizontally disposed banks of tubes of substantially circular cross section and of external diameter from 0.3 to 10 cm., the distance in centimeters between the banks of tubes and between the tubes themselves being from $0.04\ k$ to $0.20\ k$, and the overall height of the cooling elements in the vessel being from 20 to 60 cm., $k$ being the number of kilos per hour of mixed cyclohexanol and cyclohexanone passing through the vessel for each square meter of cooling surface and lying within the range 10 to 60, whereby the interspacing of the cooling surfaces is such that turbulence induced by the reaction inhibits the formation of bubbles upon them.

A laboratory apparatus for practice of the invention will now be described with the aid of the accompanying drawings in which:

FIG. 1 is an axial section through a reaction vessel,

FIG. 2 is an axial section in a plane at right angles to that of FIG. 1.

The reaction vessel consists of a glass tube 1 5 cm. in diameter constricted at the base and fitted with inlet tubes for KA 2 and nitric acid 3. Ten stainless steel cooling tubes 4 each of 6 mm. external diameter pass horizontally through the tube at different heights, being accommodated and sealed into side tubes 5 by means of polythene fasteners 6. The external distance between the stainless steel tubes is 2 cm. and the heating area is 5.6 $cm^2$ per tube. Six thermocouples 7 are located at different heights in the reactor and thermostats (not shown) are arranged to stop automatically the KA feed as soon as temperatures exceed set values. Micrometering pumps are used to feed the nitric acid and KA into the reaction vessel. Cooling water is circulated through the cooling tubes 4 from the bottom to the top via interconnecting rubber tubes (not shown).

The top of the reaction vessel 1 is connected to a degasser (not shown) consisting of a horizontal glass tube through which air or nitrogen can be blown. A weir is used to control the residence time of the liquid inside the degasser and from there the liquid is collected for recovery of the oxidation products.

The whole apparatus is enclosed in an air bath at the reaction temperature to avoid heat loss into the atmosphere.

To start up the reaction nitric acid is pumped through the vessel 1 at about 4 kg/h while passing steam through the tubes 4 until the temperature rises to about 70°C. The surrounding air temperature is raised to 75°C and steam passage is then stopped. KA is then pumped in at about 200 g/h and cooling water is passed through the tubes 4. A steady reaction rate is reached, without deposition of bubbles on the tubes 4.

By measurement of the flow rates for KA, nitric acid and cooling water and the outlet and inlet temperatures of the cooling water, the overall heat transfer co-efficient for the system can be ascertained under various operating conditions.

Using this laboratory apparatus it is found that the internal cooling tubes provide much better heat transfer than external cooling loops; that the reactor temperature can be kept at 70°–75°C without any deposition of adipic acid, even when working at concentrations of up to 15 percent of adipic acid, and that subsequent gas disengagement provides no problem.

The following table illustrates operation of the apparatus described under various conditions within the scope of the invention. In all instances the temperature of reaction was 75°C and the inlet temperature of nitric acid and KA was 50°C.

controlling the reaction temperature by bringing a mixture of nitric acid with a liquid mixture of cyclohexanol and cyclohexanone, while still undergoing reaction in a vessel and thereby evolving gas, into contact with a plurality of cooling surfaces disposed within said vessel in vertically spaced formation from each other and consisting of horizontally disposed banks of tubes of substantially circular cross section and of external diameter from 0.3 to 10 cm., the distance in centimeters between the banks of tubes and between the tubes themselves being from 0.04 $k$ to 0.20 $k$, and the overall height of the cooling elements in the vessel being from 20 to 60 cm., $k$ being the number of kilos per hour of mixed cyclohexanol and cyclohexanone passing through the vessel for each square meter of cooling surface and lying within the range 10 to 60, whereby the interspacing of the cooling surfaces is such that turbulence induced by the reaction inhibits the formation of bubbles upon them.

2. The method according to claim 1 in which the mixture of cyclohexanone and cyclohexanol is produced by oxidation of cyclohexane with oxygen-containing gases, the said mixture containing from 5 to 60 percent by weight of cyclohexanone.

3. The method according to claim 2 in which the nitric acid used is of 40 to 60 percent strength by weight and in which the proportion of nitric acid to cyclohexanol and cyclohexanone is from 7:1 to 30:1 by weight.

4. The method according to claim 1 in which the

| | | | | | |
|---|---|---|---|---|---|
| KA Flow rate 'k' (kilos/hour/m² of cooling surface) | 30 | 25 | 20 | 35 | 40 |
| Nitric acid flow rate (ratio to KA flow rate) | 9.6:1 | 8.95:1 | 8.35:1 | 10.3:1 | 11.0:1 |
| Cooling water flow rate (liter/kg of KA) | 46.5 | 39.5 | 34.0 | 54.5 | 63.0 |
| Heat transfer co-efficient (KCal/hr./m²/°C | 1055 | 1050 | 1035 | 1062 | 1068 |
| Inlet temperature of Cooling water (°C) | 22 | 22 | 22 | 22 | 22 |
| Outlet temperature of cooling water (°C) | 51 | 56 | 61 | 46 | 42 |
| Maximum concentration of adipic acid without deposition (w/w) % | 15.8 | 16.4 | 17.0 | 15.2 | 14.7 |

The process has also been carried out in a reaction vessel of similar design to that described hereinbefore and illustrated in FIGS. 1 and 2 of the drawings but in which the cooling element consisted of a single bank of stainless steel tubes 60 cm. high, 275 cm. long and 150 cm. wide. The process was operated so that the parameter $k$ for this particular vessel was between 20 and 25.

I claim:

1. In a process for producing adipic acid by oxidising with nitric acid a liquid mixture of cyclohexanol and cyclohexanone, the improvement which comprises liquid mixture of cyclohexanone and cyclohexanol is produced by oxidation of cyclohexane with oxygen-containing gases and contains from 5 to 60% by weight of cyclohexanone, and in which method the said liquid mixture is passed through the vessel at a rate, $k$, of 20 to 40 kilos per hour for each square meter of cooling surface, and nitric acid of 40 to 60 percent strength by weight is mixed with the said liquid mixture in the proportion of 8:1 to 15:1 by weight, to control the reaction temperature at 70° to 75°C.

* * * * *